United States Patent
Hsieh et al.

(10) Patent No.: US 11,017,534 B2
(45) Date of Patent: May 25, 2021

(54) BLOOD VESSEL STATUS EVALUATION METHOD AND BLOOD VESSEL STATUS EVALUATION DEVICE

(71) Applicants: Acer Incorporated, New Taipei (TW); Far Eastern Memorial Hospital, New Taipei (TW)

(72) Inventors: Cheng-Tien Hsieh, New Taipei (TW); Ai-Hsien Li, New Taipei (TW)

(73) Assignees: Acer Incorporated, New Taipei (TW); Far Eastern Memorial Hospital, New Taipei (TW)

( * ) Notice: Subject to any disclaimer, the term of this patent is extended or adjusted under 35 U.S.C. 154(b) by 0 days.

(21) Appl. No.: 16/726,918

(22) Filed: Dec. 25, 2019

(65) Prior Publication Data
US 2020/0394800 A1 Dec. 17, 2020

(30) Foreign Application Priority Data
Jun. 11, 2019 (TW) .................. 108120013

(51) Int. Cl.
*G06K 9/00* (2006.01)
*G06T 7/00* (2017.01)
*A61B 6/00* (2006.01)

(52) U.S. Cl.
CPC ............ *G06T 7/0016* (2013.01); *A61B 6/504* (2013.01); *G06T 2207/20021* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 2010/0298719 A1* | 11/2010 | Kock | G06T 7/0012 600/485 |
| 2015/0126860 A1 | 5/2015 | Beymer et al. | |
| 2016/0117814 A1* | 4/2016 | Kim | G06K 9/4604 382/128 |

FOREIGN PATENT DOCUMENTS

| | | |
|---|---|---|
| CN | 101374462 | 2/2009 |
| CN | 104867147 | 8/2015 |
| TW | I250868 | 3/2006 |

* cited by examiner

*Primary Examiner* — Atiba O Fitzpatrick
(74) *Attorney, Agent, or Firm* — JCIPRNET

(57) ABSTRACT

A blood vessel status evaluation method and a blood vessel status evaluation device are provided. The method includes: obtaining at least one angiography image corresponding to a target user; selecting a target image from the angiography image; determining a blood vessel type of the target user according to a distribution status of a target blood vessel pattern in the target image; establishing a blood vessel topology structure corresponding to the target blood vessel pattern which includes information of a width of a blood vessel in the target blood vessel pattern and information of an intersection of blood vessel in the target blood vessel pattern; and automatically analyzing a blood vessel status of the target user according to the blood vessel type and the blood vessel topology structure.

12 Claims, 7 Drawing Sheets

| Scoring segment | Focus 0 | .................. | Focus 19 |
|---|---|---|---|
| 1 | T/F | .................. | T/F |
| 2 | T/F | .................. | T/F |
| ⋮ | ⋮ | .................. | ⋮ |
| 15 | T/F | .................. | T/F |

BLOOD VESSEL STATUS EVALUATION METHOD AND BLOOD VESSEL STATUS EVALUATION DEVICE

CROSS-REFERENCE TO RELATED APPLICATION

This application claims the priority benefit of Taiwan application serial no. 108120013, filed on Jun. 11, 2019. The entirety of the above-mentioned patent application is hereby incorporated by reference herein and made a part of this specification.

BACKGROUND

1. Technical Field

The disclosure relates to a physiological status evaluation technology based on image analysis, in particular, to a blood vessel status evaluation method and a blood vessel status evaluation device.

2. Description of Related Art

Along with change of the dietary habit of modern people, cardiovascular disease has been found in more and more young people. Cardiovascular occlusion may cause myocardial infarction, while acute myocardial infarction frequently causes loss of life, and therefore, keeping the angiocarpy non-occluded is urgent. Generally speaking, if cardiovascular occlusion occurs, apart from taking medicine to control the disease, cardiac catheter surgery of the cardiology department may be adopted, and a balloon is used for expanding or a stent is placed, more seriously, the coronary artery bypass surgery of the department of cardiac surgery is selected. Moreover, SYNTAX scoring is as an evaluation method for placing a stent or performing bypass surgery after the occlusion degree of heart blood vessels is evaluated by angiography. However, the SYNTAX scoring mechanism is extremely complicated, and a doctor or a docimaster needs to research and judge the blood vessel status according to the angiography image and execute a complicated scoring procedure.

SUMMARY

The disclosure provides a blood vessel status evaluation method and a blood vessel status evaluation device, which effectively increase the blood vessel status evaluation efficiency.

The embodiment of the disclosure provides a blood vessel status evaluation method, comprising: obtaining at least one angiography image corresponding to a target user; selecting a target image from the angiography image; determining a blood vessel type of the target user according to a distribution status of a target blood vessel pattern in the target image; establishing a blood vessel topology structure corresponding to the target blood vessel pattern, which comprises information of a width of a blood vessel in the target blood vessel pattern and information of an intersection of the blood vessel in the target blood vessel pattern; and automatically analyzing a blood vessel status of the target user according to the blood vessel type and the blood vessel topology structure.

The embodiment of the disclosure also provides a blood vessel status evaluation device, comprising a storage device and a processor. The storage device is used for storing at least one angiography image corresponding to a target user. The processor is coupled to the storage device and used to operate an image processing module. The processor is used for selecting a target image from the at least one angiography image. The processor is further used for determining a blood vessel type of the target user according to a distribution status of a target blood vessel pattern in the target image. The processor is further used for establishing a blood vessel topology structure corresponding to the target blood vessel pattern, which comprises information of a width of a blood vessel in the target blood vessel pattern and information of an intersection of the blood vessel in the target blood vessel pattern. The processor is further used for automatically analyzing a blood vessel status of the target user according to the blood vessel type and the blood vessel topology structure.

Based on the foregoing, after the at least one angiography image corresponding to the target user is obtained, the target image is selected from the at least one angiography image. The blood vessel type of the target user is judged according to the distribution status of the target blood vessel pattern in the target image. Moreover, the blood vessel topology structure corresponding to the target blood vessel pattern is established, to provide information of the width of the blood vessel in the target blood vessel pattern and information of the intersection of the blood vessel in the target blood vessel pattern. Then, the blood vessel status of the target user is automatically analyzed according to the blood vessel type and the blood vessel topology structure. Therefore, the blood vessel status evaluation efficiency is effectively increased.

In order to make the aforementioned and other objectives and advantages of the disclosure comprehensible, embodiments accompanied with figures are described in detail below.

BRIEF DESCRIPTION OF THE DRAWINGS

FIG. 8 is a schematic diagram of an analysis report drawn according to an embodiment of the disclosure.

DESCRIPTION OF THE EMBODIMENTS

Figure 1:
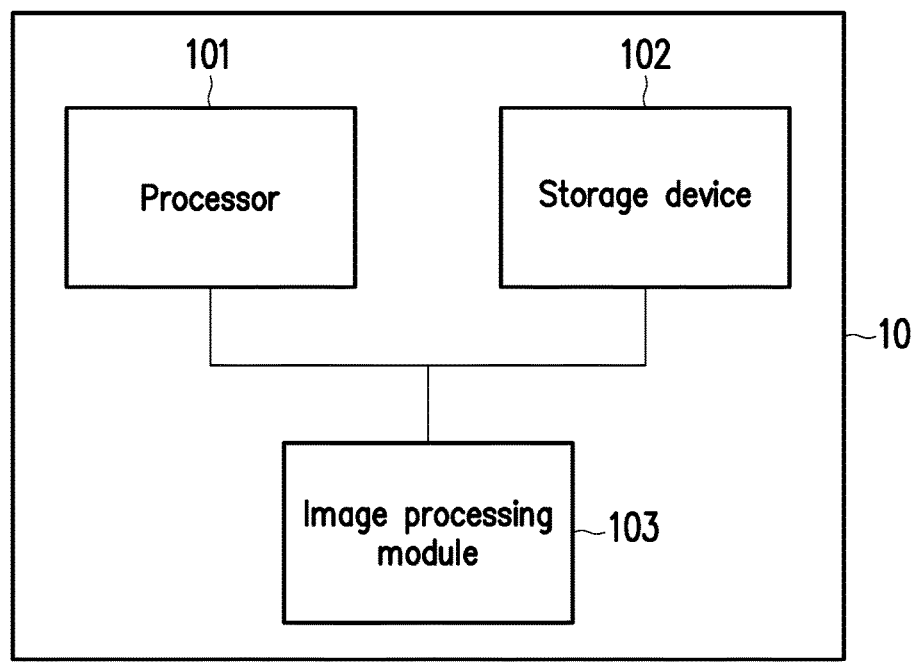
FIG. 1 is a schematic diagram of a blood vessel status evaluation device drawn according to an embodiment of the disclosure.

FIG. 1 is a schematic diagram of a blood vessel status evaluation device drawn according to an embodiment of the disclosure. Please refer to FIG. 1, in an embodiment, a device (also named as a blood vessel status evaluation device) 10 is an electronic device or a computer device with an image analysis and operation function. In another embodiment, the device 10 is also inspection equipment for cardiovascular status or image capture equipment used for angiocardiography. The device 10 is used for automatically analyzing an angiography image of a certain user (also named as a target user) and automatically generating evaluation information to reflect the blood vessel status of the target user. In an embodiment, a developing agent is injected into the heart blood vessel (for example, the coronary artery) of the target user to photograph the heart blood vessel of the target user, so as to obtain the angiography image.

The device 10 includes a processor 101, a storage device 102 and an image processing module 103. The processor 101 is coupled to the storage device 102 and the image processing module 103. The processor 101 is a central processing unit (CPU), a graphics processing unit (GPU), or other programmable microprocessors for general purpose or special purpose, a digital signal processor (DSP), a programmable controller, application specific integrated circuits (ASIC), a programmable logic device (PLD) or other similar devices or a combination of these devices. The processor 101 is in charge of the overall or partial operation of the device 10.

The storage device 102 is used for storing an image (namely, the angiography image) and other data. The storage device 102 includes a volatile storage medium and a non-volatile storage medium. The volatile storage medium includes a random access memory (RAM), while the non-volatile storage medium includes a read-only memory (ROM), a solid state disk (SSD) or a traditional hard disk (HDD) and the like.

The image processing module 103 is used for identifying and/or comparing patterns in the image by executing image processing on the image stored by the storage device 102. The image processing module 103 is used as a software module, a firmware module or a hardware module. For example, in an embodiment, the image processing module 103 includes at least one graphic processing unit (GPU) or a similar processing wafer, to execute the image processing. Or, in an embodiment, the image processing module 103 is a program code which is loaded into the storage device 102 and executed by the processor 101.

In an embodiment, the image processing module 103 does not include an artificial intelligence architecture of machine learning and/or deep learning and the like. In an embodiment, the image processing module 103 includes the artificial intelligence architecture of machine learning and/or deep learning and the like and is trained to improve the image processing performance continuously. In an embodiment, the device 10 also includes input/output devices such as a mouse, a keyboard, a display, a microphone, a loudspeaker or a network interface card, and the type of the input/output devices is not limited herein.

Figure 2:
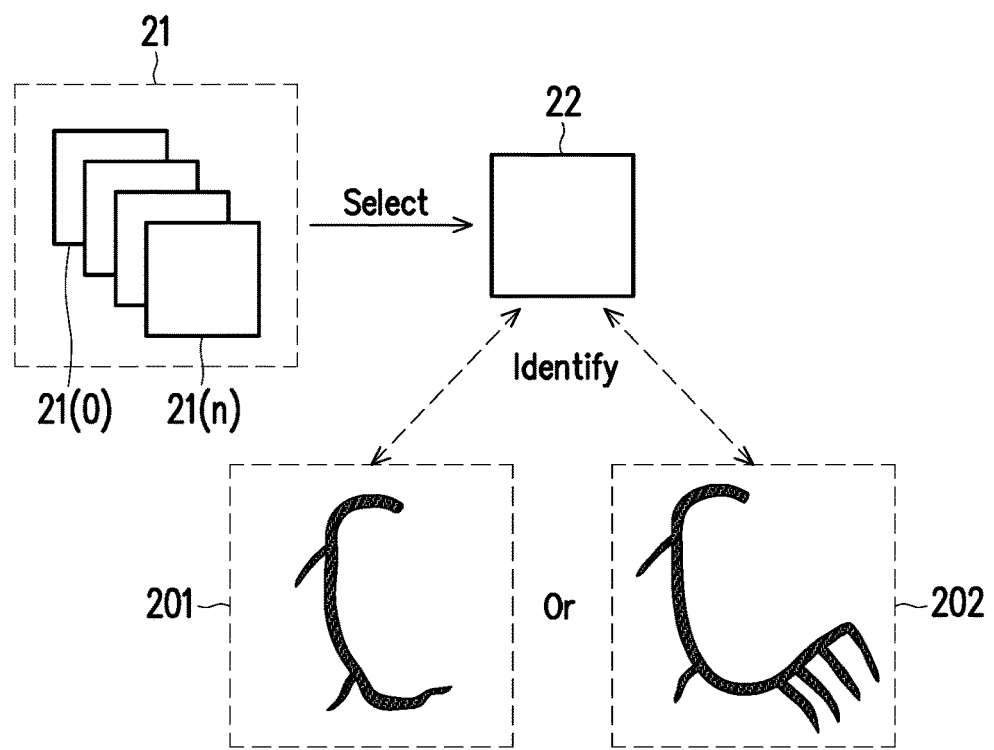
FIG. 2 is a schematic diagram of selecting a target image and determining a blood vessel type of a target user drawn according to an embodiment of the disclosure.

FIG. 2 is a schematic diagram of selecting a target image and determining a blood vessel type of a target user drawn according to an embodiment of the disclosure. Please refer to FIG. 1 and FIG. 2, in an embodiment, the storage device 102 stores multiple images 21(0)-21(n). The images 21(0)-21(n) belong to one or more film files 21. The images 21(0)-21(n) are all angiography images corresponding to the same target user. The processor 101 selects a certain image (also named as a target image) 22 from the images 21(0)-21(n).

In an embodiment, the processor 101 analyzes the images 21(0)-21(n) by virtue of the image processing module 103. According to the analysis result, the processor 101 obtains the proportion of the blood vessel pattern (also named as the first blood vessel pattern) in each of the images 21(0)-21(n). For example, such proportion includes the proportion of the blood vessel pattern in a certain image of the images 21(0)-21(n) and background pixel (or the whole image). The processor 101 selects the image 22 according to such proportion. For example, the processor selects one or more images with highest or relatively high proportion of the blood vessel pattern in the images 21(0)-21(n) as the image 22.

After the image 22 is selected, the processor 101 determines the blood vessel type of the target user according to the distribution status of the blood vessel pattern (also named as the target blood vessel pattern) in the image 22. For example, the processor 101 analyzes the image 22 by virtue of the image processing module 103, so as to identify that the blood vessel type of the target user is left dominance 201 or right dominance 202. For example, the left dominance 201 and the right dominance 202 reflect two different types of the right coronary artery. Moreover, in an embodiment, the processor 101 performs preprocessing on the image 22 by virtue of the image processing module 103, so as to obtain a relatively clear target blood vessel pattern. The target blood vessel pattern generated by preprocessing is used for subsequent image processing and analysis.

Figure 3:
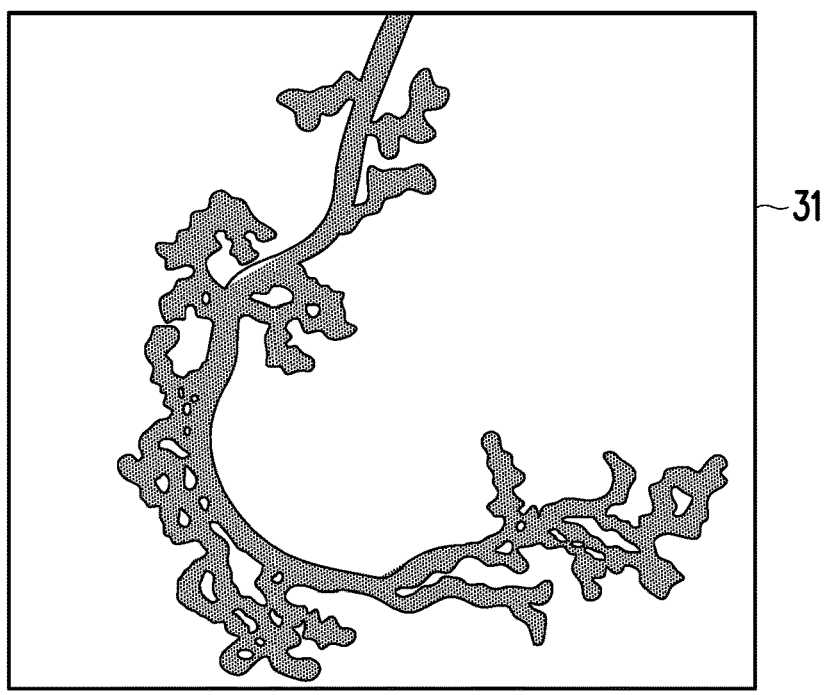
FIG. 3 is a schematic diagram of a target blood vessel pattern after preprocessing drawn according to an embodiment of the disclosure.

FIG. 3 is a schematic diagram of a target blood vessel pattern after preprocessing drawn according to an embodiment of the disclosure. Please refer to FIG. 2 and FIG. 3, the preprocessing includes execution of morphology processing, adaptive threshold processing and processing of finding the largest connected component on the image 22, so as to obtain a binarization image 31. For example, in the binarization image 31, pixel in an area marked by net bottom corresponds to bit "1" to represent a target blood vessel pattern, while the pixel of the background (the white part) corresponds to the bit "0" to be separated from the target blood vessel pattern.

In an embodiment, the processor 101 divides the target image into multiple image areas. Then, the processor 101 determines that the blood vessel type of the target user is the left dominance 201 or the right dominance 202 according to the distribution status of the target blood vessel pattern in these image areas.

Figure 4:
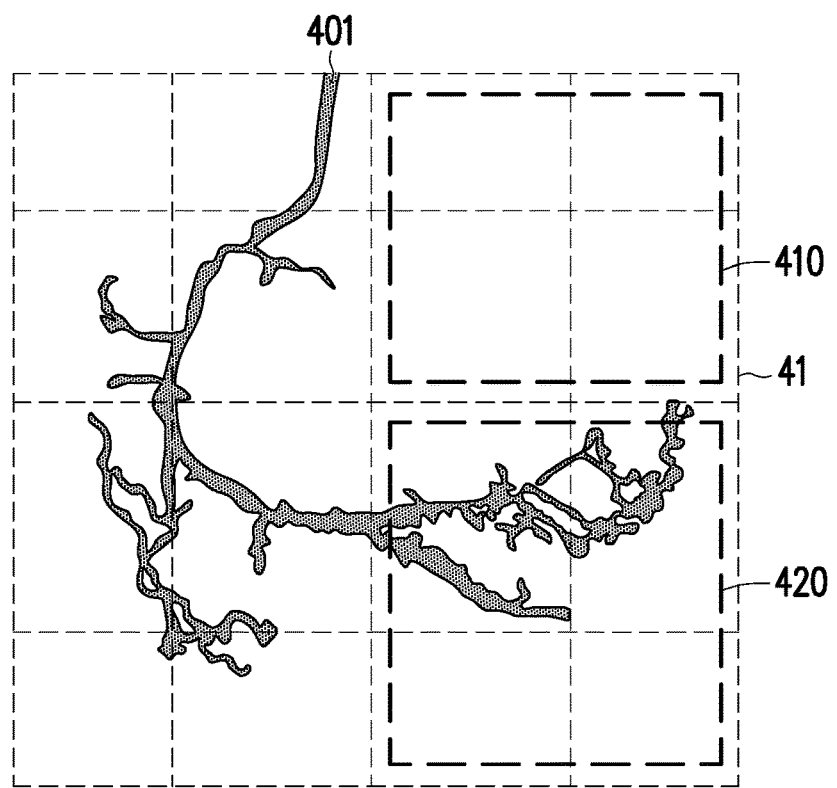
FIG. 4 is a schematic diagram of forming multiple image areas through division drawn according to an embodiment of the disclosure.

FIG. 4 is a schematic diagram of forming multiple image areas through division drawn according to an embodiment of the disclosure. Please refer to FIG. 4, an image 41 is used for representing a target image (the image 22 of FIG. 2). The image 41 is divided into multiple image areas. For example, these image areas are arranged in a form of a grid shape, as shown in FIG. 4. However, in another embodiment, the divided image areas also have other shapes and/or are arranged in other forms, which is not limited in the disclosure. Whether the blood vessel type of the target user is the left dominance or the right dominance is decided according to the distribution status of the target blood vessel pattern 401 in these image areas.

In an embodiment, the processor 101 judges whether the proportion of the target blood vessel pattern in certain image areas in the target image is higher than (or lower than) a preset value and determines the blood vessel type of the target user according to the judgement result. FIG. 4 taken as an example, the processor 101 judges whether the proportion of the target blood vessel pattern 401 in the image area (also named as the first image area) 410 of the right upper half part in the image 41 is smaller than a first preset value and/or judges whether the proportion of the target blood vessel pattern 401 in the image area (also named as the second image area) 420 of the right lower half part in the image 41 is greater than a second preset value. If the proportion of the target blood vessel pattern 401 in the image area 410 is smaller than the first preset value and the proportion of the target blood vessel pattern 401 in the image area 420 is not greater than the second preset value, the processor 101 judges that the blood vessel type of the target user is the left dominance 201 of FIG. 2. Or, if the proportion of the target blood vessel pattern 401 in the image area 410 is smaller than the first preset value and the proportion of the target blood vessel pattern 401 in the image area 420 is greater than the second preset value, the processor 101 judges that the blood vessel type of the target user is the right dominance 202 of FIG. 2. Moreover, if the proportion of the target blood vessel pattern 401 in the image area 410 is not smaller than the first preset value, the processor 101 judges that the target image is not correct and other images are re-selected as the target image.

On the other hand, according to the target image, the processor 101 establishes a blood vessel topology structure corresponding to the target blood vessel pattern. Such blood vessel topology structure includes information of a width of a blood vessel in the target blood vessel pattern and information of an intersection of the blood vessel in the target blood vessel pattern. Moreover, such blood vessel topology structure also includes other useful information, which is not limited in the disclosure.

Figure 5:
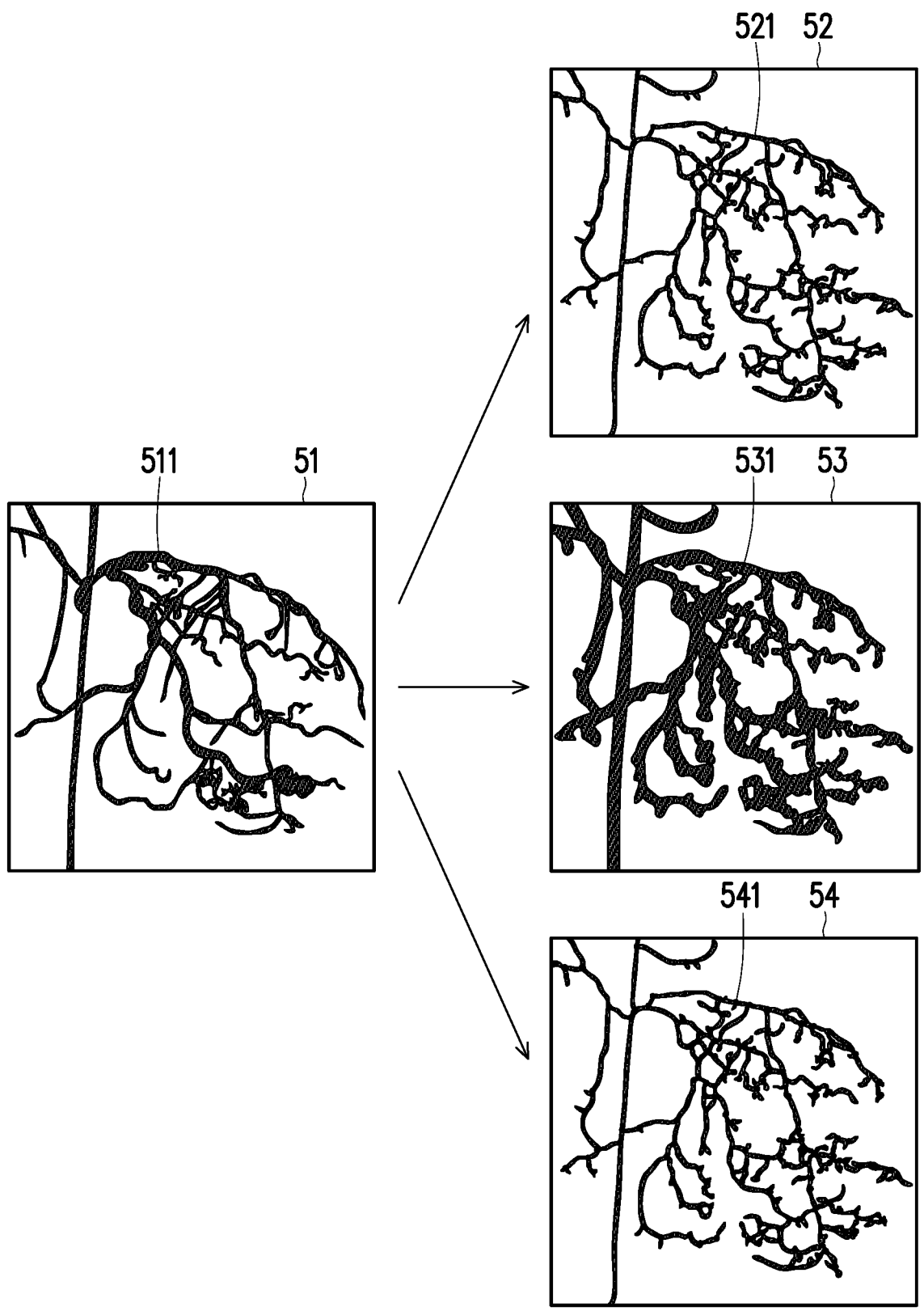
FIG. 5 is a schematic diagram of a blood vessel topology structure drawn according to an embodiment of the disclosure.

FIG. 5 is a schematic diagram of a blood vessel topology structure drawn according to an embodiment of the disclosure. Please refer to FIG. 1 and FIG. 5, an image 51 replaces the target image. The processor 101 analyzes the target blood vessel pattern 511 in the image 51 by virtue of the image processing module 103, so as to obtain images 52-54. The image 52 reflects a skeleton of a target blood vessel pattern 511. The image 53 reflects an outline 531 of the target blood vessel pattern 511. The image 54 reflects at least one intersection 541 of the blood vessel in the target blood vessel pattern 511.

In an embodiment, the processor 101 obtains the width of at least one blood vessel in the target blood vessel pattern 511 according to an interval between the skeleton 521 and the outline 531. For example, the processor 101 compares the skeleton 521 with the outline 531 to obtain a width between the skeleton 521 and the outline 531 one by one, and further obtain the width of at least one blood vessel in the target blood vessel pattern 511.

In an embodiment, the processor 101 filters the skeleton 521 in the image 52 by using at least one intersection model. For example, such intersection model includes a T-shaped intersection model, a Y-shaped intersection model and an X-shaped intersection model, etc., so as to identify at least one type of intersection in the skeleton 521. The processor 101 obtains the intersection 541 of the blood vessel in the target blood vessel pattern 511 according to the filtering result.

After obtaining the blood vessel type of the target user and the blood vessel topology structure, the processor 101 automatically analyzes the blood vessel status of the target user according to the blood vessel type and the blood vessel topology structure. For example, the processor 101 determines a scoring rule according to the determined blood vessel type. The scoring rule corresponds to one of the left dominance 201 and the right dominance 202 of FIG. 2. The processor 101 divides the blood vessel topology structure into multiple scoring segments according to the scoring rule. Then, the processor 101 evaluates the blood vessel status of the target user according to the occlusion status of the target blood vessel pattern in these scoring segments.

Figure 6:
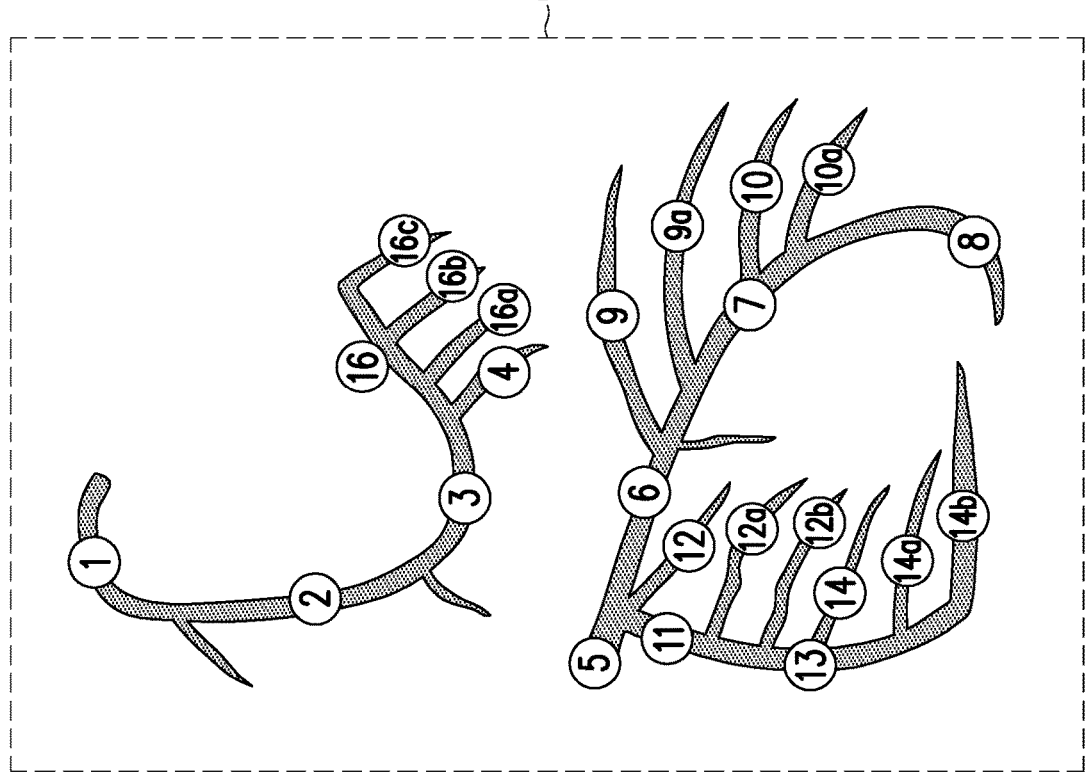
FIG. 6 is a schematic diagram of scoring segments corresponding to different scoring rules drawn according to an embodiment of the disclosure.
Figure 6:
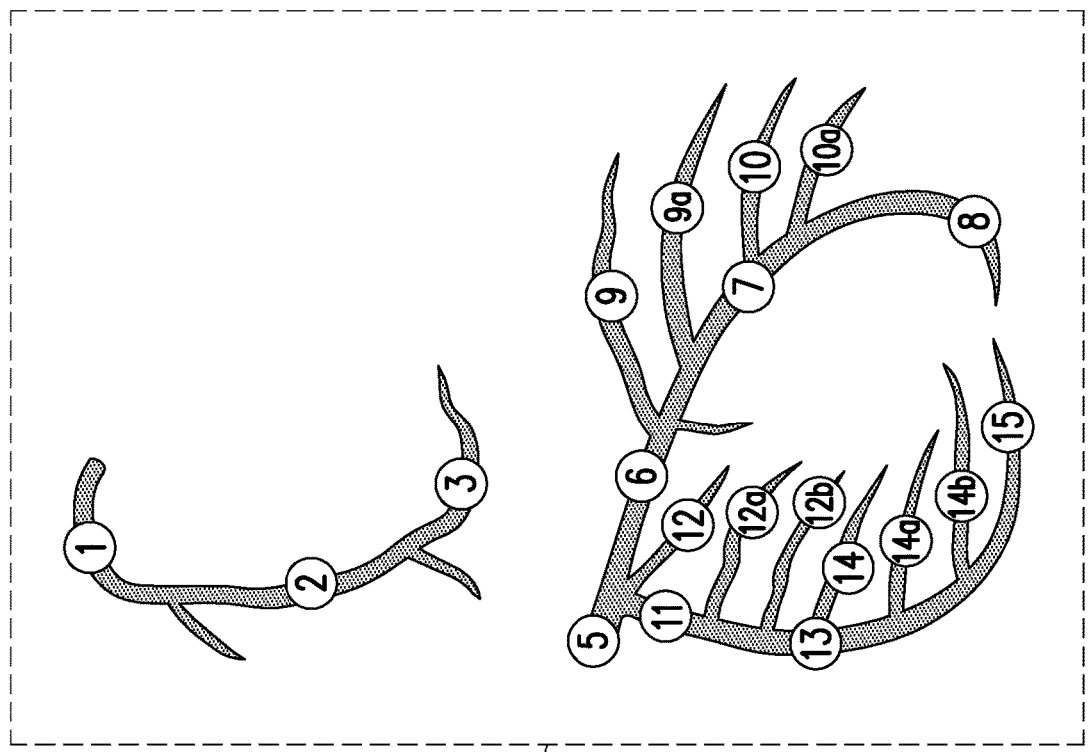

FIG. 6 is a schematic diagram of scoring segments corresponding to different scoring rules drawn according to an embodiment of the disclosure. Please refer to FIG. 2 and FIG. 6, the determined blood vessel type is the left dominance 201, and then one scoring rule (also named as a first scoring rule) 61 is adopted, so as to score the occlusion status of blood vessels in the multiple scoring segments marked with numerical values 1-15. Or, the determined blood vessel type is the right dominance 202, and then another scoring rule (also named as a second scoring rule) 62 is adopted, so as to score the occlusion status of blood vessels in the multiple scoring segments marked with numerical values 1-15, 16 and 16a-16c.

Figure 7:
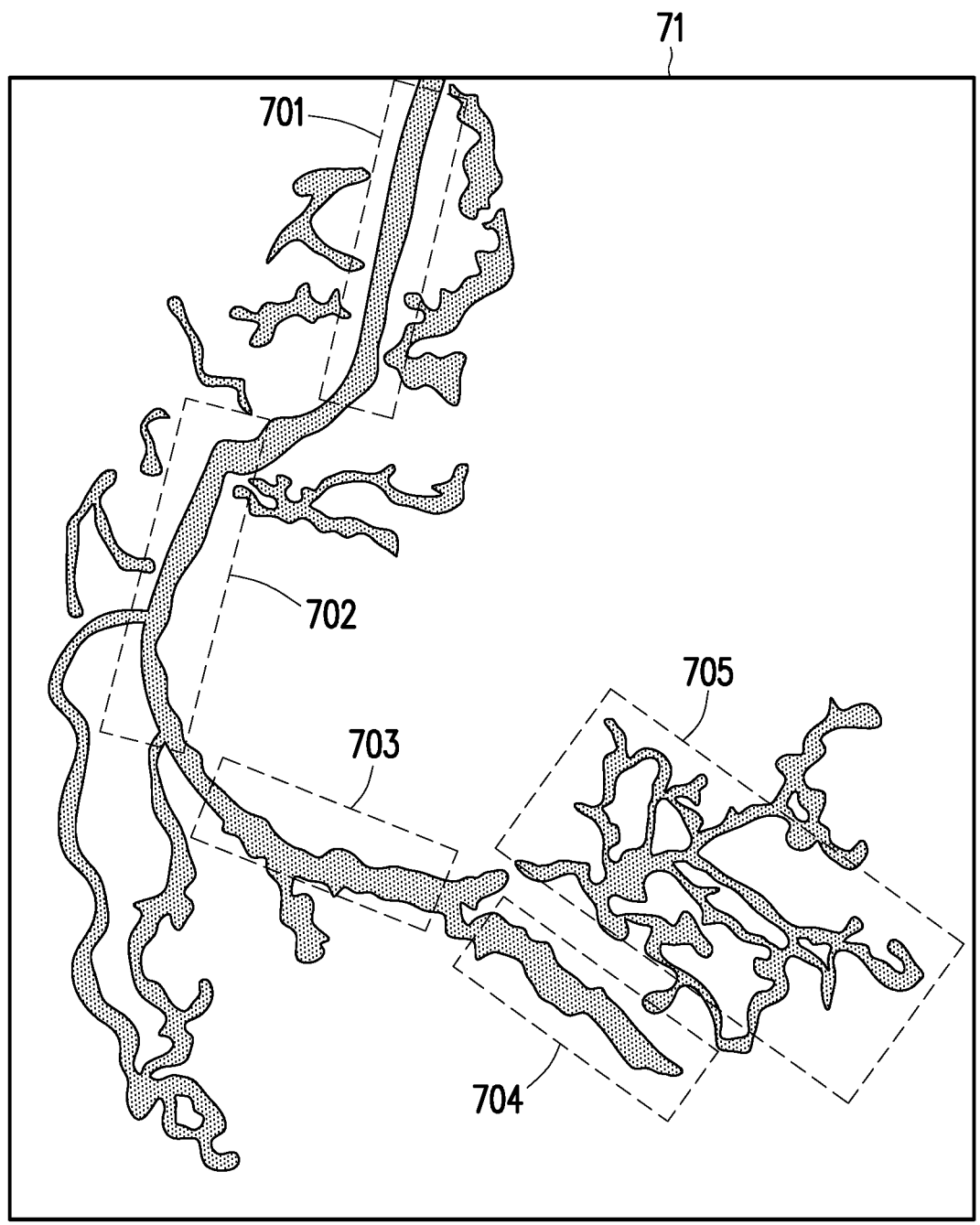
FIG. 7 is a schematic diagram of forming the scoring segments through division drawn according to an embodiment of the disclosure.

FIG. 7 is a schematic diagram of forming the scoring segments through division drawn according to an embodiment of the disclosure. Please refer to FIG. 6 and FIG. 7, with the right dominance taken as example, after the blood vessel type of the target user is determined to be the right dominance, the scoring rule 62 is adopted. According to the scoring rule 62, the target blood vessel image (or the blood vessel topology structure corresponding to the target blood vessel image) in an image 71 (that is, the target image) is divided into scoring segments 701-705. A scoring segment 701 corresponds to a segment 1 indicated by the scoring rule 62, a scoring segment 702 corresponds to a segment 2 indicated by the scoring rule 62, a scoring segment 703 corresponds to a segment 3 indicated by the scoring rule 62, a scoring segment 704 corresponds to a segment 4 indicated by the scoring rule 62, while a scoring segment 705 corresponds to the segments 16, 16a-16c indicated by the scoring rule 62. Then, the occlusion status of blood vessels in the scoring segments 701-705 is analyzed, so as to evaluate the blood vessel status of the target user. Moreover, if the target image is an angiography image close to the left main coronary artery, the left anterior descending branch and the left circumflex artery of the heart of the target user, division of the scoring segments is performed on the target blood vessel image (or the blood vessel topology structure) according to the segments 5-15 indicated by the scoring rules 61 or 62.

In an embodiment, the processor 101 analyzes the width and/or occlusion degree of the blood vessel in a certain scoring segment by virtue of the image processing module 103. The blood vessel status of the target user is determined according to the analysis result. For example, the processor 101 analyzes whether focuses such as total occlusion, trifurcation, bifurcation, aorto-ostial lesion, severe tortuosity or heavy calcification occur to the blood vessel in a certain scoring segment according to the information of the width and the information of the intersection of the blood vessel presented in the images 52-54 in FIG. 5. These focuses are, for example, defined in a SYNTAX scoring standard. The processor 101 generates evaluation information according to the analysis result, so as to reflect the blood vessel status of the target user.

FIG. 8 is a schematic diagram of an analysis report drawn according to an embodiment of the disclosure. Please refer to FIG. 8, evaluation information 81 is generated according to the analysis result of the target image, and operation details of related analysis are already described in the foregoing in detail. The evaluation information 81 is stored in the storage device 102 of FIG. 1 and output (for example, presented in a display) via an input/output interface.

In the present embodiment, the evaluation information 81 records whether any one of focuses 0-19 occurs to the blood vessels in the scoring segments 1-15. If the analysis result reflects that a certain focus (for example, focus 0) occurs to the blood vessel in a certain scoring segment (for example, the scoring segment 1), an intersection field between the scoring segment and the focus (for example, the scoring segment 1 and the focus 0) is recorded as T. Or, if the analysis result reflects that a certain focus (for example, focus 19) occurs to the blood vessel in a certain scoring segment (for example, the scoring segment 2), an intersection field between the scoring segment and the focus (for example, the scoring segment 2 and the focus 19) is recorded as F. Therefore, the analysis report 81 clearly reflects the blood vessel status of the target user.

What should be noted is that, in an embodiment, the evaluation information 81 records relevance information between at least one scoring segment and at least one focus by other forms. Moreover, in another embodiment, the evaluation information 81 records more information used for describing the blood vessel status of the target user, for example, the possibility that a certain focus occurs in a certain scoring segment, and the like, which is not limited in the disclosure.

Figure 9:
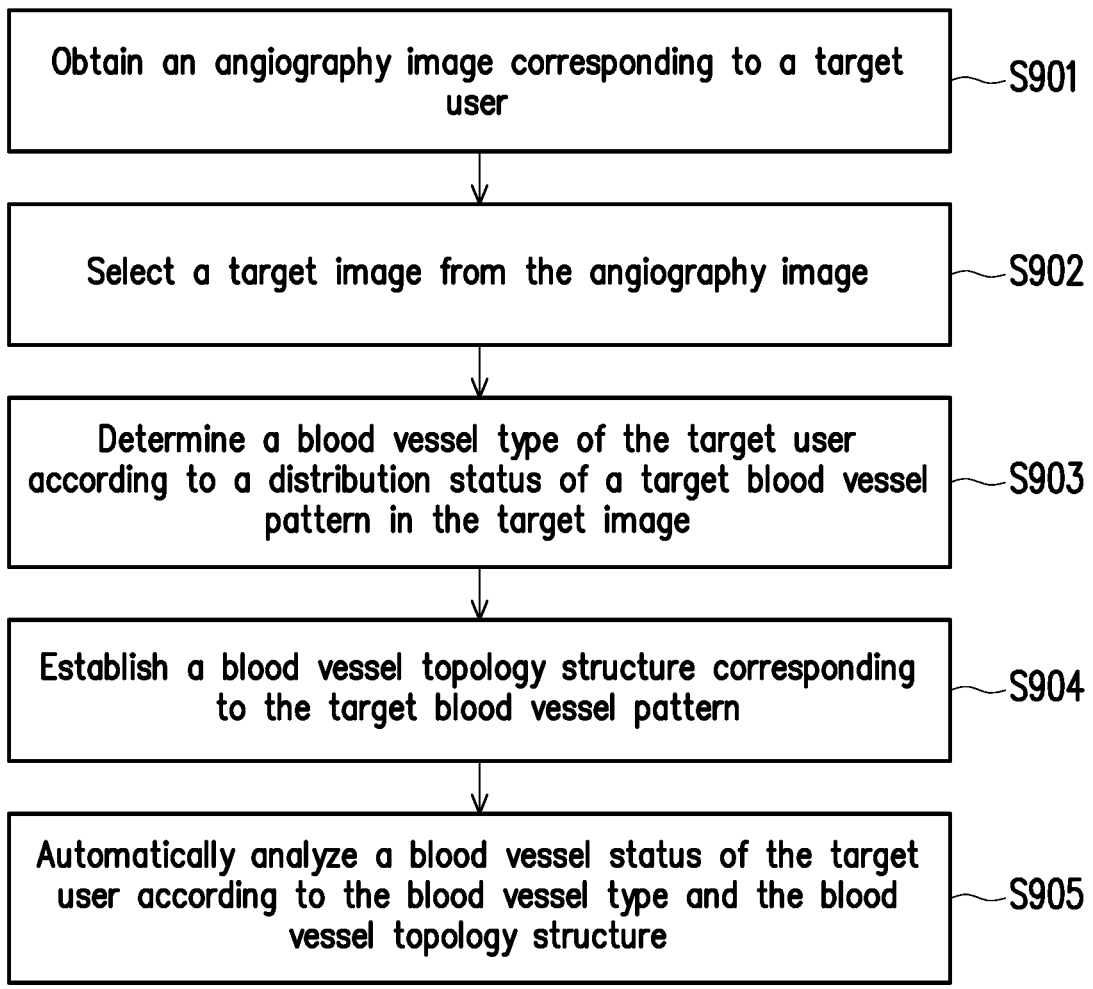
FIG. 9 is a flow diagram of a blood vessel status evaluation method drawn according to an embodiment of the disclosure.

FIG. 9 is a flow diagram of a blood vessel status evaluation method drawn according to an embodiment of the disclosure. Please refer to FIG. 9, in step S901, at least one angiography image corresponding to a target user is obtained. In step S902, a target image is selected from the at least one angiography image. In step S903, a blood vessel type of the target user is determined according to a distribution status of a target blood vessel pattern in the target image. In step S904, a blood vessel topology structure corresponding to the target blood vessel pattern is established. The blood vessel topology structure includes information of a width of a blood vessel in the target blood vessel pattern and information of an intersection of the blood vessel in the target blood vessel pattern. In step S905, a blood vessel status of the target user is automatically analyzed according to the blood vessel type and the blood vessel topology structure.

However, each step in FIG. 9 has already been described in details as above, and will not be further described herein. It is worth noting that, each step in FIG. 9 is taken as multiple program codes or circuits, which is not limited in the disclosure. Moreover, the method of FIG. 9 is used in match with the foregoing examples and embodiments, and is also independently used, which is not limited in the disclosure.

Based on the foregoing, after at least one angiography image corresponding to the target user is obtained, the target image is selected from the at least one angiography image. The blood vessel type of the target user is judged according to the distribution status of the target blood vessel pattern in the target image. Moreover, the blood vessel topology structure corresponding to the target blood vessel pattern is established, to provide information of the width of the blood vessel in the target blood vessel pattern and information of the intersection of the blood vessel in the target blood vessel pattern. Then, the blood vessel status of the target user is automatically analyzed according to the blood vessel type and the blood vessel topology structure. Therefore, the blood vessel status evaluation efficiency is effectively increased.

In an embodiment, the blood vessel status evaluation method does not belong to a medical method. For example, in an embodiment, the blood vessel status evaluation method is executed by a general user without related medical treatment background by virtue of a special device (for example, the blood vessel status evaluation device) to generate the corresponding evaluation information. Such evaluation information reflects the possible physiological status of the user for reference for the user. Moreover, in an embodiment, the blood vessel status evaluation device is also used by personnel (for example, doctors or docimasters) having related medical treatment background, to provide assistant inspection information.

Although the disclosure is described with reference to the above embodiments, the embodiments are not intended to limit the disclosure. A person of ordinary skill in the art may make variations and modifications without departing from the spirit and scope of the disclosure. Therefore, the protection scope of the disclosure should be subject to the appended claims.

What is claimed is:

1. A blood vessel status evaluation method, comprising:
   obtaining at least one angiography image corresponding to a target user;
   selecting a target image from the at least one angiography image;
   determining a blood vessel type of the target user according to a distribution status of a target blood vessel pattern in the target image;
   establishing a blood vessel topology structure corresponding to the target blood vessel pattern, which comprises information of a width of a blood vessel in the target blood vessel pattern and information of an intersection of the blood vessel in the target blood vessel pattern; and
   automatically analyzing a blood vessel status of the target user according to the blood vessel type and the blood vessel topology structure.

2. The blood vessel status evaluation method according to claim 1, wherein selecting the target image from the at least one angiography image comprises:
   obtaining a proportion of a first blood vessel pattern in a first image of the at least one angiography image; and
   selecting the target image from the at least one angiography image according to the proportion.

3. The blood vessel status evaluation method according to claim 1, wherein determining the blood vessel type of the target user according to the distribution status of the target blood vessel pattern in the target image comprises:
   dividing the target image into multiple image areas; and
   determining that the blood vessel type of the target user is left dominance or right dominance according to the distribution status of the target blood vessel pattern in the multiple image areas.

4. The blood vessel status evaluation method according to claim 1, wherein establishing the blood vessel topology structure corresponding to the target blood vessel pattern comprises:
   obtaining a skeleton of the target blood vessel pattern;
   obtaining an outline of the target blood vessel pattern; and
   obtaining the width of the blood vessel in the target blood vessel pattern according to an interval between the skeleton and the outline.

5. The blood vessel status evaluation method according to claim 4, wherein establishing the blood vessel topology structure corresponding to the target blood vessel pattern further comprises:
   filtering the skeleton by using an intersection model; and
   obtaining the intersection of the blood vessel in the target blood vessel pattern according to a filtering result.

6. The blood vessel status evaluation method according to claim 1, wherein automatically analyzing the blood vessel status of the target user according to the blood vessel type and the blood vessel topology structure further comprises:
   determining a scoring rule according to the blood vessel type;
   dividing the blood vessel topology structure into multiple scoring segments according to the scoring rule; and
   evaluating the blood vessel status of the target user according to an occlusion status of the target blood vessel pattern in the multiple scoring segments.

7. A blood vessel status evaluation device, comprising:
   a storage device storing at least one angiography image corresponding to a target user; and
   a processor coupled to the storage device and operating an image processing module,
   wherein the processor selects a target image from the at least one angiography image,
   the processor further determines a blood vessel type of the target user according to a distribution status of a target blood vessel pattern in the target image,
   the processor further establishes a blood vessel topology structure corresponding to the target blood vessel pattern, which comprises information of a width of a blood vessel in the target blood vessel pattern and information of an intersection of the blood vessel in the target blood vessel pattern, and
   the processor further automatically analyzes a blood vessel status of the target user according to the blood vessel type and the blood vessel topology structure.

8. The blood vessel status evaluation device according to claim 7, wherein an operation that the processor selects the target image from the at least one angiography image comprises:
   obtaining a proportion of a first blood vessel pattern in a first image of the at least one angiography image; and
   selecting the target image from the at least one angiography image according to the proportion.

9. The blood vessel status evaluation device according to claim 7, wherein an operation that the processor determines the blood vessel type of the target user according to the distribution status of the target blood vessel pattern in the target image comprises:
   dividing the target image into multiple image areas; and
   determining that the blood vessel type of the target user is left dominance or right dominance according to the distribution status of the target blood vessel pattern in the multiple image areas.

10. The blood vessel status evaluation device according to claim 7, wherein an operation that the processor establishes the blood vessel topology structure corresponding to the target blood vessel pattern comprises:
    obtaining a skeleton of the target blood vessel pattern;
    obtaining an outline of the target blood vessel pattern; and
    obtaining the width of the blood vessel in the target blood vessel pattern according to an interval between the skeleton and the outline.

11. The blood vessel status evaluation device according to claim 10, wherein the operation that the processor establishes the blood vessel topology structure corresponding to the target blood vessel pattern further comprises:
    filtering the skeleton by using an intersection model; and
    obtaining the intersection of the blood vessel in the target blood vessel pattern according to a filtering result.

12. The blood vessel status evaluation device according to claim 7, wherein an operation that the processor automatically analyzes the blood vessel status of the target user according to the blood vessel type and the blood vessel topology structure further comprises:
    determining a scoring rule according to the blood vessel type;
    dividing the blood vessel topology structure into multiple scoring segments according to the scoring rule; and
    evaluating the blood vessel status of the target user according to an occlusion status of the target blood vessel pattern in the multiple scoring segments.

* * * * *